(12) United States Patent
Lerner

(10) Patent No.: US 6,410,046 B1
(45) Date of Patent: *Jun. 25, 2002

(54) ADMINISTERING PHARMACEUTICALS TO THE MAMMALIAN CENTRAL NERVOUS SYSTEM

(75) Inventor: Eduard N. Lerner, Amsterdam (NL)

(73) Assignee: Intrabrain International NV, Curacao (AN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 154 days.

(21) Appl. No.: 09/197,133

(22) Filed: Nov. 20, 1998

Related U.S. Application Data

(63) Continuation-in-part of application No. 09/077,123, filed on May 20, 1998, and a continuation of application No. PCT/EP96/05086, filed on Nov. 19, 1995.

(51) Int. Cl.[7] .......................... A61F 13/00; A61F 2/00; A61K 9/00

(52) U.S. Cl. .................. 424/434; 424/400; 424/427; 424/428; 514/853; 514/854; 514/912

(58) Field of Search ................. 514/853, 854, 514/912; 424/434, 427, 428, 400

(56) References Cited

U.S. PATENT DOCUMENTS

| | | | | |
|---|---|---|---|---|
| 4,564,016 A | * | 1/1986 | Maurice et al. | 128/645 |
| 4,883,660 A | * | 11/1989 | Blackman et al. | 514/255 |
| 5,169,384 A | * | 12/1992 | Bosniak et al. | 604/20 |
| 5,545,617 A | * | 8/1996 | Dartt et al. | 514/12 |
| 5,897,858 A | * | 4/1999 | Haslwanter et al. | 424/78.04 |

FOREIGN PATENT DOCUMENTS

SU  992075  *  1/1983

* cited by examiner

*Primary Examiner*—Thurman K. Page
*Assistant Examiner*—Todd D. Ware
(74) *Attorney, Agent, or Firm*—Jerry Cohen; Perkins, Smith & Cohen, ll

(57) ABSTRACT

A device, methods and pharmaceutical compositions are disclosed for transnasal or transocular drug delivery to the central nervous system using a combination of electrotransport or phonophoresis with chemical permeation enhancers.

9 Claims, 2 Drawing Sheets

ADMINISTERING PHARMACEUTICALS TO THE MAMMALIAN CENTRAL NERVOUS SYSTEM

CROSS-REFERENCE TO RELATED APPLICATIONS

This applicant is a continuation in part of U.S. patent application Ser. No. 09/077,123, filed May 20, 1998, entitled DEVICE FOR ENHANCED DELIVERY OF BIOLOGICALLY ACTIVE SUBSTANCES AND COMPOUNDS IN AN ORGANISM and a continuation of PCT/EP96/05086 filed Nov. 19, 1995.

STATEMENT REGARDING FEDERALLY SPONSORED RESEARCH OR DEVELOPMENT

Not Applicable

FIELD OF THE INVENTION

The present invention relates to a device for the combined use of electrotransport or phonophoresis with a chemical permeation enhancer in order to facilitate transnasal or transocular drug delivery to the nervous system of a mammal.

BACKGROUND OF THE INVENTION

A variety of routes currently exist for delivering drugs with a therapeutic and/or diagnostic effect on a mammalian organism, herein termed "drugs", to the nervous system of a mammal. Examples of such routes include, among possible others, oral administration, transcutaneous or transmucosal absorption, as Ill as intravenous, subcutaneous or intramuscular injections. All of these routes of drug delivery are based on the administration of a drug into the general bloodstream, wherein the drug is delivered by the bloodstream systemically to all organs and tissues. Because all of the body organs are exposed to relatively high concentrations of a drug during systemic delivery, there is a potential for adverse effects and iatrogenic complications that may be quite severe with It is very important to consider the anatomy of the olfactory region of a mammal including human. The olfactory area is quite different between primates and lower animals. The anatomy of the nasal passages is quite complex (human nasal cavity is illustrated in FIG. 1; Anthony Wexler, personal communications). The olfactory fissure leading to the cribriform plate at the roof of the nose is very narrow; ranging from complete closureto 3–4 mm when a decongesting agent is used (Guilmette, R. A., Wicks, J. D. and Wolff, R. K., Morphometry of Human Nasal Airways In Vivo Using Magnetic Resonance Imaging, J. Aerosol Med., Vol. 2, No. 4, pp. 365–377, 1989). It is obvious that a drug-containing device in a liquid or semi-liquid form will be preferred to enter such a difficult to access region and to make an intimate contact with the olfactory mucosa in every part of the olfactory region including the olfactory fissure and the cribriform plate. certain drugs. This problem of systemic side effects can be particularly aggravated when drugs must be given relatively frequently and/or few therapeutic alternatives exist.

When a drug has to be delivered to the central nervous system (CNS), it is first administered into the systemic bloodstream. Once the drug has been distributed throughout the bloodstream, it has to penetrate a complex system of tight endothelial junctions in the capillaries supplying the CNS comprising the so-called blood-brain barrier (BBB). The blood capillaries of the BBB are relatively impermeable to large molecules, particularly the charged, polar or ionizable ones. Thus, the BBB serves the function of keeping the environment of central nervous system constant and preventing potentially harmful molecules from passing from the bloodstream through the BBB into the CNS. HoIver, many useful drugs are unable to efficiently penetrate the blood-brain barrier and reach therapeutic concentrations in the CNS. Yet others create therapeutic levels in the CNS only when their concentration in the bloodstream is increased to dangerously high levels, which leads to increased incidence of severe adverse effects, such as liver damage or kidney failure. There are also drugs that penetrate the BBB relatively Ill but cause severe systemic side effects on other organs when administered in the general bloodstream even at low concentrations.

Many drugs have a net charge, or have a polar structure, or are ionizable, or have a large molecular size. As a result, any of these drugs are unable to efficiently penetrate biological membranes (largely composed of hydrophobic lipids) including those comprising the superficial protective layer termed epidermis, or mucous membranes such as nasal mucosa. HoIver, even uncharged and non-polar drugs may be significantly impeded in their transport across the BBB if, for example, the drug tends to form a large molecular complex with itself or with other molecules in the bloodstream such as albumin protein. In order to facilitate the delivery of drugs with poor penetration potential, several approaches of physical or chemical enhancement have been proposed.

For the purpose of this invention, "electrotransport" is defined as any form of electrically assisted delivery of a substance through a mammalian tissue, such as nasal mucosa, at least partially induced or enhanced by the application of an electrical potential. Thus, the term "electrotransport" as used herein includes without limitation previously defined terms such as iontophoresis, electrotransport, iontokinesis, electroporation and electroosmosis, and the combination of, which comprises the transport of a substance (either charged or neutral) at least partially induced or enhanced by the application of an electric potential, as in U.S. Pat. Nos. 5,298,017, 5,736,580, 5,749,847. In any given electrotransport process, hoIver, more than one of these processes may be occurring simultaneously to a certain extent. In the present disclosure, the term "electrotransport" is used in its broadest possible interpretation so that it includes the electrically induced or enhanced transport of a biomolecular agent, which may be charged or uncharged, or a mixture thereof, regardless of the specific mechanism(s) of transport. A drug can therefore travel into and across the nasal mucosa, and/or across cell membranes into the olfactory nerve terminals, and/or through the cribriform lamina (located at the roof of the nose in the olfactory region) and across soft tissues along the olfactory pathway, and/or into the cerebrospinal fluid (CSF). For example, the term electrotransport as used herein includes without limitation electroporation folloId by iontophoresis and/or electroosmosis, or iontophoreses and/or electroosmosis folloId by electroporation.

The term "phonophoresis" as used here is defined without limitation as any form of transport of a substance through mammalian tissue induced or enhanced by the application of ultrasound. The biomolecular agent can thereby travel into or across the treated tissue, and/or across the cell membrane into the cell, and/or across the nuclear membrane into the nucleus. For examples of ultrasound enhancement of drug delivery see U.S. Pat. Nos. 4,948,587 and 4,767,402 the disclosures of which are incorporated herein by reference in their entirety.

As described in U.S. Pat. No. 5,023,085 the disclosures of which are incorporated herein by reference in their entirety, iontophoresis can be combined with the use of a chemical or biological agent enhancing transdermal flux to achieve an increased efficiency of drug delivery across the skin for both topical and systemic drug delivery. As described in U.S. Pat. No. 5,624,898 the disclosures of which are incorporated herein by reference in their entirety, some lipophilic substances can augment the passive absorption of a limited group of neurologic agents from nasal cavity into olfactory nerve terminals with subsequent neuronal transport to the brain. In addition, PCT Patent Application PCT/EP96/05086 of Nov. 21, 1996 (WO 97/18855, published May, 29 1997) the disclosures of which are incorporated herein by reference in their entirety, discloses a drug delivery system that employs iothophoresis or phonophoresis in order to enhance drug transport, whereas a drug can be delivered from the nasal cavity directly into the CNS, without entering the general blood circulation, through the olfactory pathway, or through the sclera or cornea of the eyeball and via the ocular neural pathway. This approach is neither topical nor systemic, but rather involves delivery of a drug from the nasal cavity or an ocular surface area to a remote site in the CNS. Thus, the disclosed system provides a high efficiency enhancement of drug delivery to the CNS and allows controlling the rate of drug administration. HoIver, in some circumstances, this approach results in a new problem of causing local damage to the tissues directly underlying the active electrode created by a large amount of current and/or the extended duration of electrotransport necessary to deliver a therapeutic amount of a drug to the CNS.

This problem is further aggravated by the fact that the nasal mucosa in general and the olfactory neuroepithelium in particular are much more delicate and susceptible to damage than skin. Furthermore, the olfactory neuroepithelium is a very specialized type of epithelium that has a limited surface area and a poor regeneration potential. For these reasons, it is very important to use the loIst possible electrical potential and current density, and to deliver the least amount of current, as Ill as to limit the duration of electrotransport. HoIver, when this is done in an attempt to limit tissue damage and patient discomfort, the efficiency of drug delivery is greatly decreased and the therapeutic value of the treatment is similarly reduced.

Thus, none of the methods disclosed in the patents referenced above results in a combination of high efficiency and low side effects delivery of drugs to the CNS. Therefore, there still exists a need to further optimize enhanced delivery of drugs to the CNS. As a result, the present invention focuses on the use of electrotransport or phonophoresis (as defined above) in combination with at least one or more chemical permeation enhancer, which greatly increases the efficiency of drug delivery, and/or decrease the potential side effects. A chemical permeation enhancer may be chosen from a large group of substances know to those skilled in the art, including but not limited to transmucosal or transdermal flux enhancers, substances that promote the absorption of a drug through the olfactory epithelium and into the olfactory neural system, substances that promote transscleral or transcorneal drug penetration, substances that facilitate the transport of a drug along the olfactory or visual pathway, substances that specifically target the CNS, or any particular region within the CNS, or peripheral olfactory or visual neural systems, as Ill as any possible combination of the above substances.

Already in 1740 Pivati introduced iontophoresis to treat arthritis and the general systemic effects of the physical enhancement technique was first observed by Munch in 1879 when strychnine killed his test animal. In the beginning of the 20$^{th}$ Century Leduc performed his famous experiments that demonstrated the potential of iontophoresis as drug delivery technique.

At present, iontophoresis as a non invasive drug delivery technique is being used in many areas of medicine like anesthesiology, pediatrics, general and orthopedic surgery, dentistry, dermatology, physical therapy, otolaryngology, and ophthalmology. Dermatologists use iontophoresis in the treatment of hyperhidrosis, plantar warts, lichen planus, scleroderma, infected burn wounds and for inducing local skin anesthesia. Physical therapists used corticosteroid iontophoresis to treat bursitis and other musculoskeletal disorders. Lidocaine iontophoresis has been successfully used by ear nose throat specialists as a local anesthetic treatment of the ear. Dentists use iontophoresis to deliver sodium fluoride, methylprednisolone in the treatment of hypersensitive teeth. More recently ophthalmologists have successfully achieved local anesthesia for short-term eyelid surgery. Also antibiotics have been delivered into the eyes by means of iontophoresis.

Due to the many iontophoresis applications, there were many (several hundreds) types of iontophoresis electrodes described and disclosed throughout the 20$^{th}$ Century. Each electrode is adapted to its specific use. It is evident that an electrode used in dentistry, will not be appropriate to deliver antibiotics through the cornea of the eye, though the mechanism principle of iontophoresis is in all these electrodes the same: transport of ionized compounds as a result of an externally applied electric field.

The presently disclosed method is based on nasal iontophoresis, in order to discriminate intranasal iontophoresis, for local treatment or for systemic delivery of medicaments through the respiratory nasal epithelium directly into the systemic circulation from nasal delivery via the olfactory mucosa directly into the CNS, Applicant preferred to use the term transnasal iontophoresis to indicate the long distance transfer of drugs from the nose to the brain.

In contrast to drug delivery through the respiratory epithelium of the nasal cavity, Applicant's method is based on drug delivery through the olfactory epithelium of the nasal cavity. Systemic nasal drug delivery implicates that drugs are delivered through the respiratory epithelium of the nasal cavity. This epithelium is easy accessible by means of nose drops and nasal sprays. However the major reason why respiratory epithelium is the target site of nasal drug administration is its rich underlying vascular network, especially in the Kiesselbach's area. These blood vessels can be accessed immediately following absorption and blood flow distributes the drug throughout the rest of the body. Vascularization in the olfactory region is much less compared to the anterior part of the nasal cavity.

The respiratory epithelium or respiratory mucosa covers the wall of the large central portion of the nasal passages. It is a highly vascular pseudostratified columnar tissue, which is constituted of three principal cell types including columnar cells, goblet cells and basal cells (Geurkink 1983, *J. Allergy Clin.Immunol.,,* 72,123–128). Ciliated columnar cells are the predominant cells, although non-ciliated columnar cells also exist in this region. The cilia beat in wave- like motion that moves the mucous and any particles therein to the posterior nasal cavity. The cilia are surrounded by tiny microvilli, which also aid in maintaining the flow of the mucous layer. Mucous secreting goblet cells are also columnar in shape and have microvilli on their surface. Basal cells sit on the basal membrane along with many columnar and goblet cells, but they do not extend up to the mucosal surface of the epithelium.

The mucous layer of the respiratory epithelium is lined with a layer of clear mucous that is in constant motion due to the powerful movements of the cilia present in the respiratory region. The mucous layer is removed and replaced about every ten minutes.

The olfactory epithelium or olfactory mucosa is a pseudostratified columnar neuroepithelium, which is comprised of three principal cell types including receptor or olfactory cells, supporting cells and basal cells. The cell type that differentiates olfactory epithelia from other types of epithelia is the receptor cell or also known as the primary olfactory neuron (cranial nerve I). They are elongated columnar like bipolar cells, which have cell bodies located at various depths within the neuroepithelium. Within the neuroepithelium, the receptor cell vesicles are rod-shaped, but at the mucous surface the diameter expands becoming knob-like, and many long immotile dendritic cilia filled with protoplasm extend into and are surrounded by the mucous. The supporting cells are covered with microvilli and extend from the mucous surface of the neuroepithelium to the basal membrane. The basal cells of the olfactory mucosa are similar in position to those in the respiratory epithelium. Unlike the basal cells in the respiratory epithelium, these cells further differentiate to become receptor cells (Graziadei P. P. C. and Monti-Graziadei, 1985, Ann.NY.acad.Sci.,457, 127–145)

Unlike the respiratory epithelium, the mucous layer in the olfactory epithelium does not have motile cilia to facilitate flow. Instead, the mucous layer is viscous and stationary, being removed from the surface only by over production by the mucous glands in the epithelium.

| Characteristic | respiratory epithelium | olfactory epithelium |
| --- | --- | --- |
| mucous layer | Dense, high renewal rate Pinkish tinge | thicker, viscous, low renewal rate. Yellowish tinge |
| Principal epithelial cell types | 1. columnar cells, ciliated with microvilli 2. goblet cells with microvilli 3. basal cells | 1. neural receptor cell, ciliated 2. supporting cells with microvilli 3. basal cells |
| Cilia | motile, coordinated movement | mature cilia are immotile, no coordinated movement |
| Principal contributors mucous secretions | goblet cells; mucous and serous glands and Lacrimal glands | Bowman glands with mucous and serous cells |
| epithelial pH | 5.5–6.5 (adults) | not available |

Therefore, it is an object of the present invention to provide an efficient and safe means for drug delivery to the nervous system that allows an optimal therapeutic concentration of a drug to be created in the nervous system of a mammal. Another object of the invention is to provide a reliable method of drug delivery that combines the use of both physical and chemical enhancement methods in order to facilitate drug transport to the nervous system from a remote site corresponding to a distal ending of a neural pathway. Yet another object of the invention is to combine the use of electrotransport or phonophoresis with a variety of chemical permeation enhancers in order to provide the desired physical and chemical enhancement of drug delivery. Still another object of the invention is to use these methods for the enhanced delivery of drugs to the nervous system of a mammal through the transnasal or transocular pathways.

SUMMARY OF THE INVENTION

The efficient and safe delivery of therapeutic amounts of a drug into the nervous system can be achieved by combining the use of a physical enhancement means with at least one or more chemical permeation enhancers. Specifically, the use of a combination of either electrotransport or phonophoresis or both with a chemical permeation enhancer increases the amount of a drug delivered to the nervous system of an individual with feIr and less prominent side effects. The drug delivered by the method of the disclosed invention can be any suitable substance that has an effect on the organism of the recipient, including, but not limited to, traditional pharmaceuticals and therapeutics, nutritional supplements and vitamins, as Ill as nucleic acids, peptides and other macromolecules. Using the methodology of the disclosed invention, drugs are delivered to the CNS via transnasal or transocular rout.

Therefore, the combined use of electrotransport or phonophoresis with a chemical permeation enhancer results in a significant enhancement of the ability to deliver a drug to the CNS. As a result, lesser amounts of the drug can be used initially, which results in a reduction in cost which may be significant particularly in case of expensive drugs such as nucleic acids and peptides. In addition, the duration of the delivery procedure can be shortened, and lesser amount of electrical charge or ultrasound applied is needed to effectuate the use of electrotransport or phonophoresis respectively in order to deliver the desired amount of drug, thus resulting in feIr and less pronounced side effects. These modifications will result in the improvement of patient's comfort which will increase his compliance with treatment. The use of electrotransport or phonophoresis provides an efficient mechanism for controlling the rate of drug delivery, which is difficult to achieve with a chemical permeation enhancer alone. In this way, the disadvantages of the prior art can be overcome.

Other objects, features and advantages will be apparent from the following detailed description of preferred embodiments thereof taken in conjunction with the accompanying drawings in which:

Figure 1A:
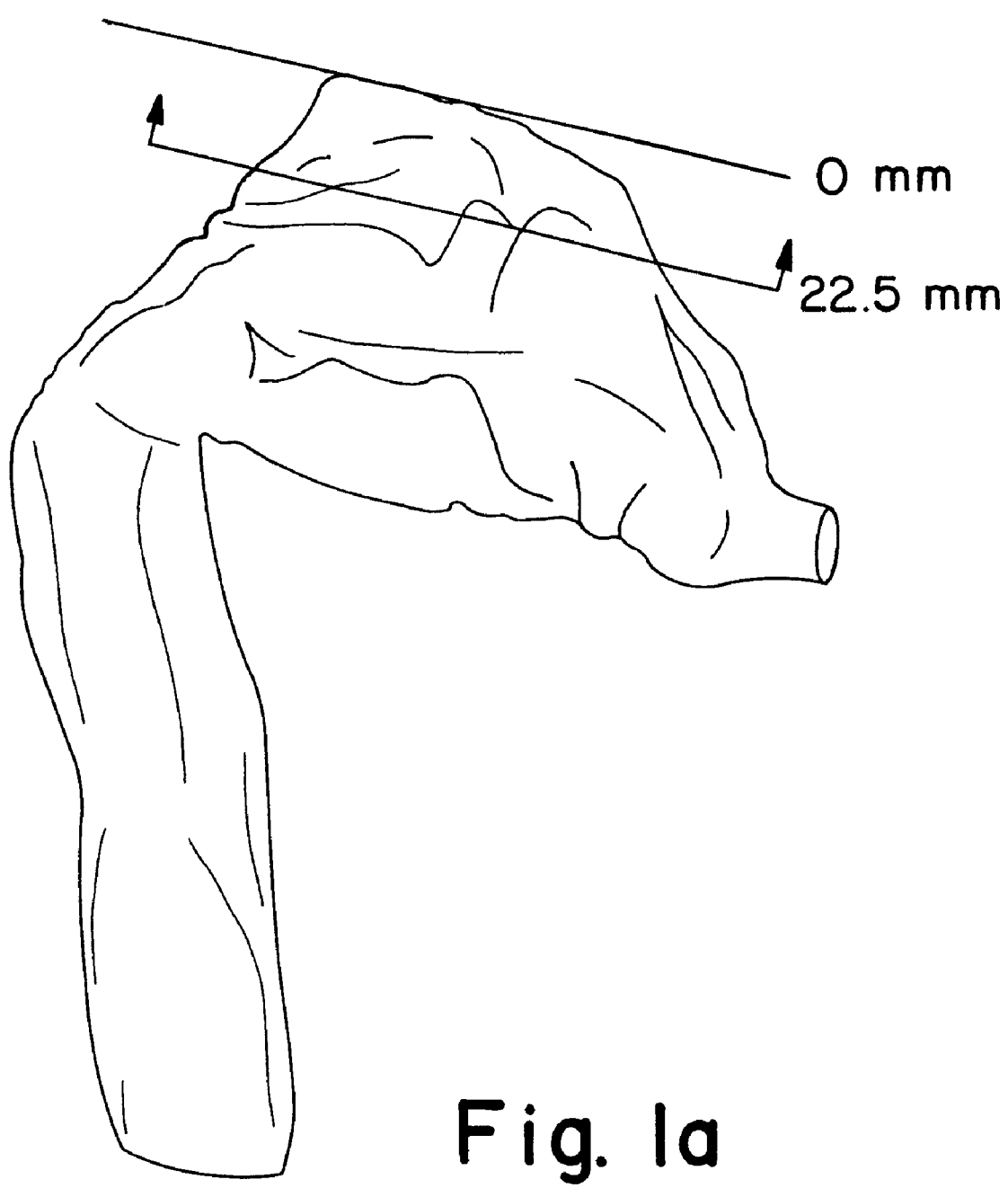
FIG. 1a: The olfactory portion of the nasal model.
Figure 2B:
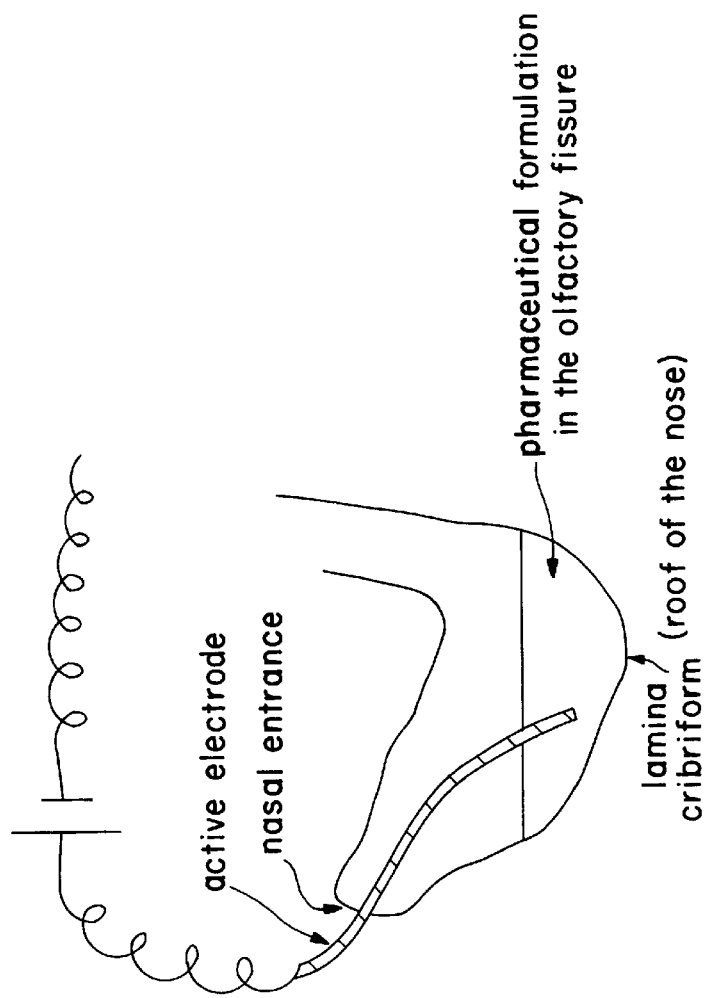
FIG. 2b: Schematic diagram of an electrode inserted into the olfactory region of the human nasal cavity.
Figure 2A:
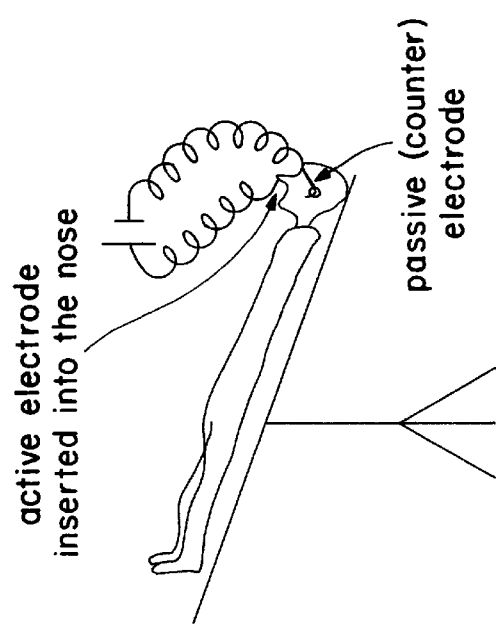
FIG. 2a: Subject with electrode inserted into the nose.

It is very important to consider the anatomy of the olfactory region of a mammal including human. The olfactory area is quite different between primate and lower animals. The anatomy of the nasal passages is quite complex (human nasal cavity is illustrated in FIGS. 1a, 2a, and 2b; Anthony Wexler, personal communications). The olfactory fissure leading to the cribriform plate at the roof of the nose is very narrow; ranging from complete closure to 3–4 mm when a decongesting agent is used (Guilmette, R. A., Wicks, J. D. and Wolff, R. K., Morphometry of Human Nasal Airways in Vivo Using Magnetic Resonance Imaging, J. Aerosol Med., Vol. 2, No. 4, pp. 365–377, 1989). It is obvious that a drug-containing device in a liquid or semi-liquid form will be preferred to enter such a difficult to access region and to make an intimate contact with the olfactory mucosa in every part of the olfactory region including the olfactory fissure and the cribriform plate.

DETAILED DESCRIPTION OF THE PREFERRED EMBODIMENTS

Applicant have found that a number of chemical permeation enhancers when used in combination with electrotransport or phonophoresis lead to a synergistic effect on the transmucosal transport of these drugs. Thus, it was found that a combination of electrotransport or phonophoresis or both with a chemical permeation enhancer leads to a much higher efficiency of transnasal drug delivery into the nervous system than was expected initially. This approach allows the use of much milder conditions for electrotransport, thus minimizing the risk of damage to the tissues involved in the drug transport. Specifically, in transnasal delivery, these milder conditions prevent damage to the nasal mucosa and particularly the olfactory epithelium, thus preserving the sense of smell. In transocular delivery, these milder conditions prevent damage to the retina and retinal pigmented epithelium, thus preserving the visual function. Also, Applicant Ire able to deliver drugs of much higher molecular Iight than with either a physical or chemical enhancement alone.

Therefore, the present invention achieves a high efficiency of drug delivery into the CNS, in particular through the nasal mucosa and the olfactory pathway, as Ill as through an ocular surface and the visual neural pathway. More specifically, the present invention relates to the use of transmucosal flux enhancers, substances that promote the penetration of a drug through the nasal epithelium into the olfactory system or an ocular surface into the visual neural system, substances that facilitate the transport of a drug along the olfactory or visual pathways and/or the surrounding tissues and fluids, substances that specifically target the CNS or any particular region within the CNS or peripheral olfactory or visual systems, as Ill as any possible combination of the above substances in conjunction with electrotransport or phonophoresis. Thus, the present invention relates to the combined use of electrotransport or phonophoresis or both with at least one or more chemical permeation enhancers for the delivery of a drug across the nasal mucosa or an ocular surface along the olfactory or visual pathway, respectively, and within the CNS. The composition may be applied intranasally preferably selectively to the olfactory epithelium located in the posterior two thirds of the nasal cavity predominantly on the nasal septum and the dorsal side of the nose (for reveiw see Guilmette, R. A. et al., J. Aerosol Med., vol. 2, No. 4, pp 365–377, 1989; Kepler, G. M. et al., Inhalation Toxicology, vol. 7, pp 1207–1224, 1995). Selective application of the composition to the olfactory area will minimize systemic absorption through the non-olfactory epithelium and will enhance the amount of drug delivered to the CNS. The pharmaceutical composition of the present invention may be administered by way of a tube or catheter, by syringe, by packtail, by pledget, using an endoscope, or by submucosal injection or infusion. The composition may be dispensed intranasally as a powdered or liquid nasal spray, nose drops, a gel, an ointment, or any other pharmaceutical formulation (could be liquid, semisolid and solid) known to those skilled in the art.

In one embodiment, the present invention combines a method of physical enhancement of drug delivery by way of electrotransport or phonophoresis with a pharmaceutical composition (or a chemical agent) that enhances the rate of transmucosal flux, whereas the said combination enhances the delivery a drug across nasal mucosa or an ocular surface, at least partly through the olfactory or visual pathway, respectively, and/or the CSF and into the CNS, or a particular region of the CNS, wherein the physical enhancement is used at reduced electric potential, current amount and density, and/or less time of tissue exposure to a physical enhancement means. This results in an increased rate of drug delivery across the nasal mucosa into the olfactory pathway, or across an ocular surface into the visual pathway, either pathway leading to the CNS.

In another embodiment of present invention, the use of a combination of a physical enhancement method, such as electrotransport or phonophoresis, with a lipophilic micelles or a liquid carrier, substantially increases the efficiency of drug delivery across the nasal mucosa into the olfactory pathway leading to the CNS, which may be also applicable to the transocular route. The physical and chemical methods of enhancement may be applied simultaneously or sequentially in any order.

The present invention allows for the reduction of time of nasal or ocular tissues exposure to the drug delivery procedure which significantly reduces patient discomfort, for example during transnasal delivery when at least one electrode or probe must be inserted deep into the nasal cavity. Also, the reduction of time of the exposure of the nasal mucosa or the ocular surface to the drug minimizes the passive absorption of the drug into the systemic blood circulation which may be prominent with the use of a chemical enhancer alone, and may cause systemic side effects. Finally, it is also highly desirable to decrease the time from the beginning of treatment to the onset of the pharmacological effect of a drug on the nervous system (which is achieved with a combination of physical and chemical enhancement disclosed here) so that it is comparable or less than the time required when the drug is given orally, which is particularly important in an acute setting when the treatment is needed emergently. The present invention also allows for the reduction of intensity of the electrical current, which minimizes the risk of damage to the very delicate nasal mucosa or to the intraocular tissues (e.g. the retina and retinal pigmented ephithelium), and also improves patient comfort and compliance with treatment. In addition, larger molecular Iight drugs may be delivered by the combined use of physical and chemical enhancement methods of the present invention.

In the method of the present invention, the use of a physical enhancement means, such as electrotransport or phonophoresis, allows to efficiently control the rate of drug delivery, which is difficult to achieve with a chemical permeation enhancer alone. In particular, the rate of drug delivery can be controlled by modulating the parameters of electrotransport or phonophoresis including, but not limited to, electrical voltage or ultrasound frequency, electrical current intensity or ultrasound intensity, the contact surface area of the electrode or the phonophoresis probe, as Ill as the duration of the exposure or the frequency of repeated episodes of the exposure to the electrical potential or ultrasound. Furthermore, electrotransport or phonophoresis provides a directional control for the drug transport, thus enhancing the efficiency of non-systemic drug delivery into the CNS through relatively remote sites such as the transnasal or transocular routes.

If electrotransport is used for the physical enhancement of drug delivery, the current intensity may range from 0.001 mA to 2 A, but preferably from 0.01 mA to 1 A, and yet more preferred 0.1 mA to 100 mA, most preferred 0.25 mA to 25 mA. The current density per unit area may range from 0.01 mA/cm$^2$ to 5 A/cm$^2$, but preferably from 0.1 mA/cm$^2$ to 1 A/cm$^2$, yet more preferred from 1 mA/cm$^2$ to 800 mA/cm$^2$, and most preferred from 2.5 mA/cm² to 500 mA/cm². It should be noted that the range of current density and/or current intensity in electrotransport-enhanced drug delivery is determined primarily by the balance of two factors. The greater the amount of charge delivered the more efficient the drug transport. And second, the higher the current density, the higher the incidence of local side effects from electrotransport such as nasal or ocular damage. HoIver, the incidence of local side effects is also inversely proportional to the duration of electrotransport. Thus, safe and acceptable current density and/or current intensity inversely depend on the duration of electrotransport. The shorter the duration of the procedure, the higher current density and/or current intensity can be tolerated.

The area of the nasal mucosa termed herein the "olfactory epithelium" or the "olfactory region" for the purpose of the disclosed invention defines without limitation the area of nasal mucosa that covers the dorsal and septal portions of the human nose, in particular the olfactory cleft and the septal mucosa of the superior and middle turbinates predominantly in the posterior and middle thirds of the nose. More precise dimensions of the olfactory region as Ill as the nasal anatomy vary betIen different animal species and humans, and betIen different subjects of the same species, and are known to those skilled in the art. Furthermore, the nasal airway dimensions can be measured in vivo for each particular subject using MRI or CT scan, and a computer-generated modeling or casting of the airway can be performed (see Guilmette, R. A. and Gagliano, T. J., Ann. occup. Hyg., vol. 38, suppl. 1, pp. 69–75, 1994; Cheng, K. H. et al., J. Aerosol Sci., vol. 27, No. 5, pp. 785–801, 1996; Guilmette, R. A., Cheng, Y. S. and Griffith W. C., Ann. occup. Hyg., vol. 41, suppl. 1, pp. 491–496, 1997).

These considerations are important because the larger the surface area of the useful interface betIen the applied pharmaceutical composition of the present invention (such area is ultimately limited by the olfactory region or by the accessible ocular surface such as cornea and sclera) the greater the amount of the transferred charge which determines the amount of the delivered drug into the olfactory or ocular pathway, respectively, and ultimately into the nervous system. In addition, a larger surface area of contact allows for a loIr current intensity which leads to less side effects from electrotransport. On the other hand, if the pharmaceutical composition comes in contact with a non-olfactory nasal region, it may create a current divergence reducing the efficiency of CNS drug delivery and increasing the amount of drug absorbed into the systemic blood stream. Excessive amounts of nasal or ocular secretions may also enhance current divergence in the disclosed method and should be reduced or blocked with an appropriate agent known to those skilled in the art.

In the preferred embodiment, electrotransport or ultrasound is applied directly to the pharmaceutical composition of interest to be transported into or through the olfactory epithelium of the nasal mucosa. Upon entering the olfactory pathway through the nasal mucosa, which is a principal barrier to the drug transport in the pathway from the nasal cavity to the brain, the drug travels further until it reaches the CNS. The mechanisms of the drug transport within the olfactory pathway may include, but are not limited to, axoplasmic transport, delivery by the cerebrospinal fluid and transport along the perineural extracellular matrix. Thus, an increased transnasal mucosal flux of a drug due to applied electric potential or ultrasound in combination with a chemical enhancer agent facilitates delivery of the drug from the nasal cavity through the olfactory pathway and into the CNS.

As an alternative approach for augmenting drug transport across the nasal olfactory epithelium, certain transdermal penetration enhancers that have been previously reported to enhance drug delivery across skin may be used (for examples, see U.S. Pat. No. 5,023,085 the disclosures of which are incorporated herein by reference in their entirety). Thus, transdermal flux enhancers known to those skilled in the art are used as adjuncts in the pharmaceutical composition of the present invention in combination with a physical enhancement means, such as electrotransport or phonophoresis in order to enhance the delivery of a drug across the nasal mucosa into the olfactory pathway and/or into the CNS.

In an alternative embodiment, electrotransport or ultrasound is indirectly applied to the pharmaceutical composition contained within a delivery device that provides a means of additional rate control, or used for the purpose of multiple refillings, or designed to provide a reproducible, consistent and relatively simple way of insertion of the said composition deep into the nasal cavity (perhaps under an endoscopic control) to the olfactory region located at the roof of the nose which is not a trivial task, or in case of the transocular approach, into the subconjunctival space. The device can be polymeric or similar in construction to transdermal patches currently in use and known to those skilled in the art. The material can be sensitive to a physical energy, including electromagnetic energy, ultrasound, thermal energy, or ionizing radiation. Thus, a physical energy can be used to control the drug transfer rate by direct interaction with the pharmaceutical composition and/or by interaction with the delivery device containing the said composition in order to facilitate the release of the drug. Also, in this embodiment, the pharmaceutical composition or any component or a combination of some of the components of the pharmaceutical composition to be used with the method of the present invention may be administered by way of a specialized reservoir associated with a physical enhancer means such electrotransport electrode or phonophoresis probe.

In the preferred embodiment, the method of the present invention includes simultaneous application of a pharmaceutical composition containing a mixture of a drug with at least one chemical permeation enhancer with physical enhancement of drug delivery using electrotransport or phonophoresis.

In an alternative embodiment, the pharmaceutical composition of the present invention or any component or a combination thereof is applied prior to the application of a physical enhancement means, such as electrotransport or phonophoresis. The pharmaceutical composition of the present invention or any component or a combination thereof may also be applied simultaneously or following the application of a physical enhancement means, such as electrotransport or phonophoresis. As an example, the nasal mucosa may be pretreated with a chemical permeation enhancer in an appropriate composition, folloId by or simultaneously with application of an electric potential to physically facilitate the transnasal delivery of the drug into the CNS. In this particular example, a drug and a chemical permeation enhancer are contained in the pharmaceutical composition applied to the nasal mucosa before the application of a physical enhancement means and alloId to act upon the mucosa on its own before the initiation of physical enhancement, or alternatively, simultaneously with physical enhancement administration such as when a drug and a chemical enhancer are contained in a reservoir associated with an electrotransport electrode or an ultrasound probe, thus both chemical and physical enhancers act at the same time.

In still another alternative embodiment, a drug is contained in both the composition containing a chemical permeation enhancer used for pretreatment of the nasal mucosa and in the composition contained in a specialized drug reservoir associated with an electrotransport electrode or an ultrasound probe. In yet another alternative embodiment, a drug is contained in the composition contained in a specialized drug reservoir associated with an electrotransport electrode or an ultrasound probe and is used following pretreatment of the nasal mucosa with a chemical permeation enhancer to increase mucosal permeability. In a further alternative embodiment, both a chemical permeation enhancer and a drug comprise a composition contained in a specialized drug reservoir associated with an electrotransport electrode or an ultrasound probe and thus are used simultaneously with physical enhancement.

The methods of the present invention are particularly suited for targeting the nervous system via the transnasal or transocular routes, and can be used to treat a disease at least partly affecting a region of the nervous system particularly the CNS, even when the disease has systemic clinical manifestations such as in certain cases of obesity. Representative drugs include, but are not limited to, those used for the treatment of neurologic and neurosurgical disorders such as Alzheimer's disease, Parkinson's disease, multiple sclerosis, age-related CNS changes, AIDS-associated dementia, seizure disorders, neural damage from trauma or a cerebrovascular disorder such as stroke, tumors of the CNS, meningitis and encephalitis. Psychiatric disorders, such as affective disorders, including depression and mania, schizophrenia, insomnia, neuroses, phobias, and chronic pain can also be treated using the methods of present invention. Drugs that target the components of the olfactory and/or the visual pathways including respectively the olfactory epithelium or the retina as Ill as other cells and tissues comprising the olfactory or visual pathways, can be delivered by these methods. For example, anosmia due to the damage to the olfactory neural pathway including the olfactory bulb, diabetic or other types of retinopathy (particularly those with a neovascular component), retinopathy of prematurity, glaucomatous optic neuropathy and age-related macular degeneration. Similarly, diseases that are at least partially caused by an abnormality or imbalance in the CNS or peripheral nervous system, such as hypertension and obesity, can be treated using these methods.

An example of a pharmaceutical composition that can be used with the methods of the present invention is as follows:

(1) a therapeutically effective amount of a drug;

(2) a pharmaceutically-appropriate carrier, that may include, but is not limited to, a stabilizer, a suspending agent, an emulsifier, a preservative, an antimicrobial, or a thickener; and (3) an aqueous or non-aqueous solvent.

The pharmaceutical composition and methods thus described are suitable for the delivery of a wide range of drugs, but preferably those with a molecular Iight of betIen 10 and 10,000,000 Daltons, more preferably betIen 50 and 500,000 Daltons, and most preferably betIen 100 and 100,000 Daltons. The preferred use of the disclosed method and the pharmaceutical composition is with ionized drugs or those capable of ionization. In particular, this method and the pharmaceutical composition may be useful with highly charged or polar molecules, those drugs with poor lipid solubility that do not penetrate biological membranes Ill, and those with medium-high molecular Iights (e.g. greater than 300 Daltons). HoIver, this method and the pharmaceutical composition can also be used with drugs that are not ionizable, including neutrally charged molecules and those non-polar in nature.

The expression "a drug" refers to any substance suitable for use in a mammalian organism and known to those skilled in the art, but preferably refers to a pharmaceutically active agent or a combination thereof that at least as part of its action targets the CNS or/and the olfactory or visual system, whereas the said agent is used for diagnosis, treatment or/and prevention of diseases with the pathogenesis involving the CNS or the olfactory or ocular system including those that have neurological, psychiatric or systemic clinical manifestations. Among the preferred drugs are nucleic acids, including genes particularly those incorporated into a vector such as a plasmid or a virus, DNA particularly cDNA, RNA particularly mRNA, DNA-RNA chimeric molecules, any type of antisense oligonucleotides particularly those with phosphothioate linkage and chimeric RNA/DNA oligonucleotides, external guide sequences for RNAse P, ribozymes, antibodies, oligopeptides, polypeptides, and proteins.

Examples of drugs that can be used with the present invention include, but are not limited to, the drugs that either increase or decrease the effects of any of the cytokines or growth factors or the like (such as neurotrophic factors and those modulating angiogenesis and vascular growth), including without limitation nerve growth factor (NGF), vascular endothelial growth factor (VEGF), ciliary neurotrophic factor (CNTF), brain-derived neurotrophic factor, fibroblast growth factor, insulin, insulin-like growth factor, glia-derived nexin, as Ill as gangliosides and phosphatylserine, extracellular matrix remodeling enzymes (such as metalloproteases) and their inhibitors (such as synthetic or tissue inhibitors of metalloproteases, SIMPs or TIMPs, respectively), integrins and their ligands. Particularly preferred are NGF, CNTF, VEGF and GM-1 ganglioside.

Conventional therapeutics are particularly preferred for use as "a drug" in the pharmaceutical composition and methods of the present invention. Examples of preferred dosages of some of these, based upon use in an adult of about 50 to 80 kg Iight, are as follows: Aspirin, 0.1 to 1,000 mg; acetominophen, 0.1 to 10,000 mg; doxazosin, 0.01 to 25 mg; indomethacin, 0.01 to 50 mg; ibuprofen, 0.1 to 1,000 mg; naproxen, 0.1 to 500 mg; piroxicam, 0.01 to 20 mg (minimal dosage derived from systemic dosage divided by 500 to 1,000). HoIver, in particular circumstances, doses outside of these ranges may be used as Ill.

When the drug is a nucleic acid, in the preferred composition it is used in an aqueous solution at any concentration, but preferably ranging from 10 ng/ml to 50 mg/ml, more preferred from 100 mcg/ml to 25 mg/ml, most preferred from 1 mg/ml to 15 mg/ml. HoIver, in another preferred composition, a drug can be used at a maximal or near maximal concentration that can be achieved in a solution since electrotransport and phonophoresis appear to be concentration-dependent. This means that the amount of a nucleic acid drug delivered into the CNS is directly proportional to its starting concentration, other conditions being equal. Thus, the higher the initial concentration of a nucleic acid drug in the disclosed pharmaceutical composition, the shorter the time required for electrotransport and/or the loIr the current intensity and density required for delivery of a particular dosage into the CNS. The shorter the time of electrotransport (or phonophoresis) or the loIr the current intensity and density, the less the incidence of the potential side effects. Alternatively, when the drug is expensive to produce in large quantities, it may be used at low concentrations, and the desired dosage will be administered over a longer period of time, or drivern by a higher current and/or current density. When the drug is a peptide, in the preferred compostion it is used at a maximal or near maximal concentration that can be achieved in an aqueous or non-aqueous solution. The amount of the delivered peptide is directly proportional to its starting concentration. HoIver, in the preferred composition, the useful concentration ranges for electrotransport delivery from 1 ng/ml to 50 mg/ml, more preferred from 100 ng/ml to 25 mg/ml, most preferred from 100 mcg/ml to 20 mg/ml. Again, a loIr concentration of a drug can be used for a prolonged delivery period, and/or with higher energy enhancement (e.g. higher current intensity and/or density for electrotransport).

The initial concentration of the drug and its delivered dose will, of course, depend upon the physiochemical and pharmacological properties of the particular drug administered the background physical condition of the patient, and particularly upon the nature, stage and severity of the medical condition to be treated or prevented. In the preferred embodiment, the pharmaceutical composition of the present invention contains one drug. In an alternative embodiment, a combination of two or more drugs may be used as Ill.

Also, a drug suitable for use with the present invention includes, without limitation, any diagnostic agents which can be used with an imaging technique such as magnetic resonance imaging (MRI), positron emission tomography (PET), computer-assisted tomography (CAT), X-Ray, fluoroscopy and single photon emission computerized tomography. Examples include without limitation gadalinium, iodine-based materials, barium and ZnAc.

The method of the present invention is particularly useful for the administration of those drugs easily degradable in the gastrointestinal tract, metabolized in an internal organ (such as the liver) or in the blood, rapidly excreted from the bloodstream (e.g. through kidney clearance), and those with poor penetration through the blood-brain or blood-ocular barrier. Also, the drugs with potential systemic side-effects will benefit from direct administration in the CNS avoiding the blood stream.

In an alternative embodiment of the pharmaceutical composition of the present invention, a drug may be physically or chemically complexed with a transmucosal or transocular permeation enhancer, such as a polycationic polymer including a chitosan, for example by a covalent or ionic linkage.

The formulation of the pharmaceutical composition of the present invention may be as a powder, granules, solution, ointment, cream, aerosol, drops or others known to those skilled in the art. The solution may be isotonic or hypotonic, sterile and otherwise suitable for intranasal or ocular administration by a drop-dispenser, or other means known to those skilled in the art.

The pharmaceutical composition of the present invention may optionally contain a variety of additional agents that decongest the nasal mucosa particularly in the olfactory area (e.g. by reducing the amount of or thinning the mucosal secretions), reduce systemic absorption of a drug into the bloodstream, optimize the efficiency of electrotransport or phonophoresis, reduce side effects, and generally improve unpleasant subjective sensations such as that of discomfort or pain. In an alternative embodiment, an additional agent can be used separately from the pharmaceutical composition, for example in order to pretreat the nasal mucosa prior to administration of a drug. For example, a nasal decongestant may be used that is capable of reducing the amount of mucous and/or thinning mucosal secretions, and enlarging the nasal passages. The nasal decongestant can be selected from the following exemplary list without limitation: cocaine (preferably total amount <200 mg), neo-synephrine (preferred 0.5%), oxomethazoline, epinephrine, and euphedrine. The nasal decongestant can be administered as a pharmaceutical composition in the form of a powdered or liquid nasal spray, nasal drops, a gel, or ointment, using any available delivery system including a tube, catheter, syringe, by packtail, by pledget, or by intrarnucosal injection. The nasal decongestant may be precisely targeted to the olfactory region using a means of direct or indirect localization control (e.g. endoscopy or X-ray).

A vasoconstrictive agent, such as epinephrine or phenylephrine may be used as an additional agent in the pharmaceutical composition of the present invention to reduce systemnic absorption of a drug. The preferred concentration of epinephrine is from 0.001 to 1 mg/ml; more preferred from 0.01 to 0.5 mg/ml, more preferred from 0.05 to 0.2 mg/ml, and most preferred is 0.081 mg/ml. Also, an anesthetic agent can be used as an additional agent in the pharmaceutical composition of the present invention to reduce or ameliorate the sensation of discomfort during the procedure. This additional agent can be any local or topical anesthetic known to those skilled in the art. The most preferred is lidocaine at a preferred concentration of 0.2 to 20%, more preferred at 1 to 10%, and most preferred at 2%. Another example is proparacaine.

Other examples of additives that optimize the efficiency of electrotransport, reduce associated side-effects, reduce absorption of the drug into the systemic blood circulation, and improve subjective comfort are described in PCT patent application PCT/EP96/05086 of Nov. 21, 1996 (WO 97/18855, published May 29, 1997) and comprise, without limitation, ions, most preferred chloride and/or sodium, organic or nonorganic buffers, epinephrine and/or topical anesthetics, most preferred lidocaine.

In an alternative embodiment, the pharmaceutical composition of the present invention contains either a modified drug or an additional substance that facilitates transport of the drug along the olfactory or visual pathway to the CNS, as Ill as those that target the drug to a particular area of the olfactory or visual systems, or to a certain area of the CNS such as the brain stem or a particular region within it. Examples include, but not limited to, receptors, receptor ligands, signaling molecules, biologically active peptides, leader sequences, and lipophillic moeties.

The expression "pharmaceutically-appropriate carrier" refers to any material which is otherwise pharmaceutically appropriate and compatible with other ingredients of the composition, e.g. a drug. The carrier may be either in liquid, solid or semi-solid form. It is preferred that the carrier is isotonic or hypotonic with nasal or ocular fluids, depending on the route of administration, and is within the range of pH 4.0–9.0 with a preferred range of 4.5–8.0 in order to avoid local irritation and damage to nasal mucosa or ocular surface. Importantly, the pH may be adjusted for each particular drug in order to optimize the efficiency of electrotransport that depends on the net charge of the drug that is influenced by the surrounding pH.

The expression "aqueous solvent" refers to water itself (preferably deionized), a water-based buffering solution, or a solvent which comprises a water-miscible organic solvent such as methanol, ethanol, isopropyl alcohol, propylene glycol, polyethylene glycol or glycerin. The expression "non-aqueous solvent" refers to a liphophilic solvent including, but not limited to, dimethylsulfoxide (DMSO).

In the preferred embodiment of the pharmaceutical composition of the present invention, chemicals that enhance the permeation of drugs across mucosal membranes can be added to the composition. Chemical permeation enhancers comprise any suitable compound that increases permeation across the nasal mucosa or an ocular surface to a drug via any suitable mechanism. They preferably include, but not limited to, cell envelope disordering compounds, solvents, steroidal detergents, bile salts, chelators, surfactants, nonsurfactants, fatty acids, and mixtures thereof. Chemical permeation enhancers may be used separately or in combination.

Nonlimiting examples of chemical permeation enhancers that can be used with the pharmaceutical composition of the present invention with disclosed methods are as follows:

(1) Polycationic polymers, including polycationic carbohydrates, the most preferred being diethylaminoethyl-dextran (DEAE-dextran) and chitosans as Ill as their derivatives with any degree of acetylation and any molecular light as Ill as their pharmaceutically appropriate salts, but most preferred is N-trimethyl chitosan chloride. Useful polycationic polymers are listed in U.S. Pat. No. 5,744,166. The polycationic polymers preferably have a molecular light of 5,000 or more Daltons, more preferably at least 50,000–500,000 Daltons, and most preferably 500,000 Daltons or more. The chitosan or its derivatives preferably have an intrinsic viscosity of at least 400 ml/g, most preferably from 500 to 1000 ml/g, in an aqueous solvent. Preferably, the concentration of a polycationic polymer in aqueous solution is from 0.01 to 50% light/volume (w/v), more preferably from 0.1 to 30% w/v, most preferably from 0.25 to 15% w/v.

(2) Chelators including EDTA, sodium caprate, sodium salicylate, decanoylcarnitine, sodium taurodihydrofusidate as Ill as their derivatives. Preferred concentrations for sodium salicylate are 50 mM to 2M, and for sodium taurodihydrofusidate are 0.5 mM to 50 mM.

(3) Long-chain acylcamitines (12–18 carbon fatty acid esters), most preferably palmitoylcarnitine at any concentration but most preferred from 0.05 mM to 0.8 mM. Also included in this group are isopropyl myristate, methyl laurate, oleyl alcohol, glycerol monoleate, glycerol dioleate, glycerol monosterate, glycerol monolaurate, propylene glycol monolaurate, sodium dodecyl sulfate, and sorbitan esters and mixtures thereof.

(4) Calcium-modulators, but most preferably verapamil.

(5) Cyclodextrins and their derivatives most preferred are dimethyl-beta-cyclodextrin and randomly methylated beta-cyclodextrin. The preferred concentrations of cyclodextrins are from 0.1% to 20% w/v.

(6) Bile salts most preferred is a steroidal detergent selected from the group including natural and synthetic salts of cholanic acid, surfactants, lysophosphatidylcholine and phospholipids, laureth-9, and mixtures thereof.

(7) A transmucosal flux enhancing amount of a transdermal penetration enhancer. An exemplary list of preferred epithelial penetration enhancers includes organic compounds selected from the group consisting of C2 or C3 alcohols, C3 or C4 diols, 1-alkylazacycloheptan-2-one, said alkyl having from 8 to 16 carbon atoms, or a cis-olefin of the formula:

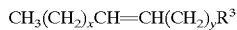

where $R^3$ is $CH_2OH$, $CH_2NH_2$, or $COR^4$, and $R^4$ is OH or $(C_1-C_4)$ alkoxy, x and y are each an integer from 3 to 13 and the sum of x and y is from 10 to 16. The most preferred epithelial penetration enhancers in pharmaceutical composition B are cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoicacid, cis-12octadecenoic acid, cis-5-eicosenoic acid, cis-9-eicosenoic acid, cis-11-eicosenoic acid, cis-14-eiosenoic acid, 1-decylazacycloheptan-2-one, 1-dodecylazacycloheptan-2-one or 1-tetradecylazacycloheptan-2-one. Out of these, most preferred is oleic acid.

(8) A lipophilic adjuvant that promotes the absorption of a drug into the peripheral olfactory nerve terminals. The lipophilic adjuvants may be used as micelles, separately or in combination with a physical enhancement means of the present invention. Preferred lipophilic adjuvants are gangliosides; most preferred GM-1 ganglioside and phosphatidylserine.

Additional substances that enhance permeability of mucosal membranes and/or an ocular surface are known to those skilled in the art and can be used in the pharmaceutical composition of the present invention.

In addition, chemical permeation enhancers or other substances may be used to facilitate solubilization of drugs, particularly those with poor water solubility such as lipophilic compounds, as Ill as oligopeptides, large polypeptides, and nucleic acids including oligonucleotides and large DNA or RNA molecules. The preferred substances that can be used to facilitate water solubility of a drug are cyclodextrins and their derivatives, most preferred are dimethyl-beta-cyclodextrin or randomly methylated beta-cyclodextrin.

In the preferred embodiment of the present invention, the pharmaceutical composition is contained in a drug reservoir directly associated with an active electrode (could be either the anode or cathode) for electrotransport or an ultrasound probe. Electrotransport or phonophoresis provide an active transport means to rapidly and effectively transport the drug out of the drug reservoir to the nasal mucosa or to an ocular surface, and further to the nervous system. The drug reservoir may be disposable and designed for a single use, whereas it contains a particular dosage of a drug in an appropriate pharmaceutical composition, suitable for administration with the method of the present invention preferably under particular predetermined conditions such as duration of administration, current or ultrasound intensity, current or ultrasound density, specified for each particular drug. The conditions of administration may vary depending on the nature, severity and acuteness of the disease to be treated. The drug reservoir may be chosen from many known to those skilled in the art. Specific examples include without limitation a gel such as a hydrogel, a hollow container such as a pouch or cavity, a porous sponge or pad.

In another embodiment, the drug reservoir is directly connected to an active electrode of an electrotransport device or to an ultrasound probe in order to provide a renewable source of the pharmaceutical composition containing a drug. In addition, electrotransport delivery systems typically have an independent electrical polr source, e.g. one or more batteries, and/or an electrical controller designed to regulate the flow of electric current through the electrodes and, thereby, the rate of drug delivery. The active and counter electrodes are connected to opposite poles of the polr source. Alternatively, the necessary polr may be supplied, at least in part, by a galvanic couple formed by the contact of two electrodes made of dissimilar materials known to those skilled in the art.

In the preferred embodiment of the method of the present invention, the active electrode or the ultrasound probe is applied as a double copy simultaneously into both nostrils or onto both eyes. So there are two active electrodes (or ultrasound probes) one applied in each nostril or on the surface of each eye. In another embodiment, the electrode (or the probe) is inserted only in one nostril (or onto one eye) at a time, which improves the subject's breathing function in case of transnasal delivery, and increases the level of comfort. In the single electrode method, the electrode (or the probe) may be alternatively inserted into either nostril, or always in the same nostril that for some reason is preferred (better anatomical access to the olfactory region e.g. due to a deviated nasal septum).

The use of physical enhancement means for transnasal drug delivery to the CNS has the obvious disadvantages of having to insert an electrode or a probe deep into the nose where the width of the olfactory fissure in humans on the average is about 0.5–2.0 mm. Thus, it is difficult to design an electrode or a probe that would fit such dimensions and would be easy enough to use, particularly when self insertion by the patient is preferred. This is further aggravated by the fact that an electrode or a probe has to have a drug reservoir for the drug to be administered which also expands the overall dimensions and complicates the design. In addition, the use of physical enhancement, such as electrical current has a risk of local adverse effects such as electrical, thermal or mechanical damage to the nasal mucosa and particularly the olfactory epithelium that mediates the sense of smell. Also, the nasal mucosa can be easily traumatized by a hard object resulting in bleeding, or can sIll and obstruct the nasal air passage causing discomfort for the patient. All this considered, a delivery system that avoids a physical enhancement means (such as electrical potential or ultrasound) and the associated equipment such as electrodes and probes, respectively, would have the advantage of being safer, easier to use, as Ill as easier to design and to manufacture.

If a drug is administered into the nose in a formulation with poorly defined mucosal contact surface area, such as liquid, powder, microspheres or ointment, it will contact not only olfactory epithelium but also other areas of nasal mucosa (see U.S. Pat. No. 5,624,898). This fact has at least two major disadvantages making this approach practically useless in clinical practice. Firstly, the absorption of drugs from the nasal mucosa into systemic bloodstream may be quite efficient and is Ill known to those skilled in the art. In fact, this route of systemic drug administration has been exploited in the past. The anterior third of the nasal cavity is the region of most efficient systemic absorption where the Kiesselbach's area rich in blood vessels is located. Unfortunately, the olfactory region is located at the roof of the nose and importantly includes the olfactory fissure extending to the cribriform lamina, the area of the nasal cavity particularly difficult to reach. Thus, a pharmaceutical formulation without a defined contact surface area corresponding to the olfactory epithelium area will have the potential of causing significant systemic absorption, alleviating the advantages of this method of drug delivery to the CNS.

Secondly, a drug-containing pharmaceutical formulation or a device with a variable or a much smaller surface area compared to the area of the olfactory epithelium may not provide sufficiently large contact area with the olfactory epithelium (which is the end-point of the olfactory pathway) for efficient drug delivery to the CNS. For example, if the drug formulation is a liquid, powder, microspheres or ointment, it may be difficult to selectively interface with the olfactory region located deep in the nasal cavity so that the drug makes contact with a large enough surface of the olfactory region for efficient delivery into the olfactory system without interfacing with non-olfactory mucosa. In addition, the area of contact may vary significantly from one application to another. Furthermore, recent imaging studies show that the olfactory region of the human nose is quite narrow in vivo and difficult to access under usual conditions.

The present invention discloses the device for drug delivery facilitated by transmucosal permeation enhancers whereas said device has a particular shape, configuration and surface area to fit into the olfactory region of the nasal cavity and to provide an adequate interface area and intimate contact with the olfactory epithelium. The preferred dimensions of the device may fluctuate slightly for different subjects and are based on the measurements of the human nasal cavity and the olfactory region in particular. Averaged measurements of the human nose or those determined for each particular subject can be utilized (for review and measurement methods see Guilmette, R. A. and Gagliano, T. J., Ann. occup. Hyg., vol. 38, suppl. 1, pp. 69–75, 1994; Cheng, K. H. et al., J. Aerosol Sci., vol. 27, No. 5, pp. 785–801, 1996; Guilmette, R. A., Cheng, Y. S. and Griffith W. C., Ann. occup. Hyg., vol. 41, suppl. 1, pp. 491–496, 1997).

The device of the present invention has a limited, relatively Ill-defined and constant surface area, which prevents a significant overlap with non-olfactory nasal mucosa particularly that in the Kiesselbach's area. Even if the shape of the device changes (e.g. if the device comprises a semi-solid or a gel-like substance), the surface area will remain constant similarly to the constant surface area of an inflated or deflated football. Also, the present invention discloses the use of a nasal decongestant with the disclosed device that has been found to significantly enlarge the nasal passages including those in the olfactory region and to facilitate the insertion and positioning of the device in the appropriate area of the nose to provide an optimal interface with the olfactory mucosa for efficient delivery into the CNS.

In the preferred embodiment, the entire device has particular dimensions and shape to fit into the olfactory fissure and to make an intimate interface with olfactory epithelium.

In an alternative embodiment, the drug transferring part of the device has particular dimensions and shape to fit into the olfactory fissure, whereas the remainder of the device which may comprise a drug reservoir is positioned in the anterior or posterior portion of the nasal cavity, or when the drug transferring part is connected to a drug reservoir located outside of the nasal cavity.

In another alternative embodiment, the device has particular dimensions and shape not to obstruct the nasal airways. Alternatively, the device contains air passage(s). Either embodiment improves the subject's breathing function and comfort.

It is very important to consider the anatomy of the olfactory region of a mammal including human. The olfactory area is quite different betIen primates and loIr animals. The anatomy of the nasal passages is quite complex (human nasal cavity is illustrated in FIG. 1). The olfactory fissure leading to the cribriform plate at the roof of the nose is very narrow; ranging from complete closure to 3–4 mm when a decongesting agent is used. It is obvious that a drug-containing device in a liquid or semi-liquid form will be preferred to enter such a difficult to access region and to make an intimate contact with the olfactory mucosa in every part of the olfactory region including the olfactory fissure and the cribriform plate.

Thus, I disclose another preferred embodiment, where the device comprises a drug dispersed in or linked to a gel-forming polymer that can be either synthetic or natural. Therefor, the pharmaceutical composition may exist in either liquid or solid state, for example a liquid pharmaceutical composition with a solidifying potential under certain conditions such as a change in temperature. For example, the pharmaceutical composition is liquid before administration but forms a gel when administered into the nasal cavity and makes contact with the nasal mucosa which creates particular conditions resulting in the pharmaceutical composition to become solid or semi-solid. Such gel-forming conditions include without limitation a particular pH preferably ranging from 6.0 to 8.5 and more preferred from 6.8 to 7.8, the body temperature in the nasal cavity whereas the pharmaceutical composition is liquid when the temperature is either higher or loIr than that in the nasal cavity, but becomes a gel when administered into the nasal cavity. In the preferred embodiment, the pharmaceutical composition is in a solid state when the temperature is in the range from 35.0° C. to 38.5° C., more preferred from 36.0° C. to 38.0° C., and most preferred from 36.4° C. to 37.4° C. (for examples of such liquid-gelling materials see U.S. Pat. Nos. 4,478,822; 4938763; 5384333; 5252318; 4188373; 5624962; 5599534; 5292516; 5306501; 53002295 the disclosures of which are incorporated herein by reference in their entirety).

It is also possible to modulate the temperature inside the nasal cavity by an external temperature source, such as a heater of a cooler (e.g. ice) applied externally to the nose or internally into the nasal cavity, or as a stream of hot or cold air or fluid in order to change the temperature of the pharmaceutical composition and thus its solid or liquid state (depending on whether it has to be administered or removed). Alternatively, the pharmaceutical composition gradually solidifies into a gel upon adding a solidifying agent which may be added immediately before or after intranasal administration (for example, polyacrylamide gradually solidifies upon addition of a combination of temed and ammonium persulfate), or when exposed to the air upon transfer of the composition from an air-protected environment into the nasal cavity. Other mechanisms for making a liquid pharmaceutical composition that solidifies in situ are obvious to those skilled in the art, and include without limitation dissolving a non-reactive polymer in biocompatible solvent to form a liquid, placing the liquid into the olfactory region of the nasal cavity and allowing the solvent to dissipate and to produce a solid or semi-solid drug releasing device (for example see U.S. Pat. No. 4,938,763 the disclosures of which are incorporated herein by reference in their entirety). It is preferred that the polymer comprising the pharmaceutical composition be biocompatible with the nasal mucosa. Also, it is preferred that the polymer be biodegradable.

In the preferred embodiment, the pharmaceutical composition provides long term or extended drug release, but may be a short term one in particular when the release of the drug from the device is controlled by additional physical or chemical means, including without limitation ultrasound, electromagnetic energy including electrotransport, light energy particularly lasers (which can be applied with endoscopic assistance), ionizing radiation, temperature, pH and/or osmolality changes, or others means known to those skilled in the art. In the preferred embodiment, the pharmaceutical composition provides continuous drug release. HoIver, the release of the drug from the device may be pulsed or intermittent in particular when the release is controlled by additional physical or chemical means (see above).

In the preferred embodiment, (the material comprising) the device has mucoadhesive properties, or is covered by a mucoadhesive film on the contact surface. In another embodiment, the material becomes mucoadhesive upon solidifying, or upon contacting the nasal mucosa and/or hydrating.

The drug delivery system of the present invention may be administered via syringe, catheter etc. to the olfactory region of the nose. An example of method of administration is when the subject is positioned so that the olfactory region is in the gravity-dependent position, for example when the subject is supine with hyperextended neck and with the foot end of bed elevated (FIG. 2). The drug delivery system in a liquid or semi-liquid form will collect under gravity in the olfactory region filling the olfactory fissure preferably up to the roof of the nose (cribriform plate), and solidify later on (e.g. upon further exposure to body temperature, or due to slowly acting solidifying agent, etc.). The method of administration includes self-administration by the subject or administration by a health professional preferably using direct or indirect visual control, e.g., by an endoscope.

The drug transferring surface of the disclosed device comprises a pharmaceutical composition-containing layer adapted to provide an intimate interface with nasal mucosa in olfactory region and to create an optimal drug transfer relationship. Examples of materials suitable for the drug-transferring surface of the present invention are multiple and are known to those skilled in the art.

Alternatively, a liquid or semi-liquid gel after it fills the olfactory area of the nasal cavity is covered over by a nonpermeable mucoadhesive film. The film adheres to the walls of the nasal cavity around the area covered by the pharmaceutical composition of the delivery system, thus securing an intimate contact of the delivery system with the nasal mucosa of the olfactory region and preventing the lateral spread of the pharmaceutical composition to the non-olfactory mucosa.

In one embodiment, the mucoadhesive drug delivery device comprises a drug reservoir and a mucoadhesive means. In an alternative embodiment, a drug can be dispersed within the mucoadhesive means. In yet another embodiment, a drug reservoir may have mucoadhesive properties or become mucoadhesive upon contact with nasal mucosa and/or hydration (e.g. a hydrogel).

Examples of the drug reservoir for the present invention include, but not limited to, a hollow container such as a pouch or cavity, a gel such as a hydrogel, microspheres, a porous sponge or pad, a polymer preferably a polycationic polymer and most preferred a chitosan or a chitosan salt or derivative, as Ill as reservoirs similar to patches presently in use for the transdermal or transmucosal drug deliver and known to those skilled in the art.

The device disclosed in the present application may be inserted as a double copy simultaneously in both nostrils. In another embodiment, the device is inserted only in one nostril at a time, which improves the subject's breathing function, and increases the level of comfort. In the latter case, the device may be alternatively inserted into either nostril, or always in the same nostril that for some reason is preferred (better anatomical access to the olfactory region e.g. due to a deviated septum).

Preferred means of physical enhancement of drug transport through the nasal mucosa and/or other tissues in the nasal-CNS pathway, or activation of drug transport from the device to the nasal mucosa are electrical potential (including iontophoresis and/or electroosmosis), ultrasound (including phonophoresis), magnetic field, temperature or ionizing radiation.

Certain references are noted and incorporated herein by reference as though set out at length herein: U.S. Pat. Nos. 5,298,017; 5,023,085; 5,624,898; 3,989,816; 4,316,893; 4,405,616; 4,537,776; 4,557,934; 5,744,166; Stoughton, Arch. Derm. v. 188, pp. 474–477 (1982); Cooper, J. Pharm. Sci., v. 73, pp. 1153–1156 (1984); Akhtesi et al., J. Pharm. Pharmacol. v. 36, p. 7P (1984); Olanoff, et al. in Chapter 22 of Methods to Enhance Intranasal Peptide Delivery in Controlled Release Technology Pharmaceutical Application, ed. Ping I. Lee and William R. Good, pp. 301–309 (American Chemical Society, 1987).

The following items A–S recapitulate some of the scope and details of the present inventions [claims pro se appear after item S of this specification portion].

A. A method of delivering a pharmaceutical composition to the nervous system of a mammal, comprising the steps of:
 (a) administering said pharmaceutical composition transnasally;
 (b) enhancing delivery of said pharmaceutical composition with a chemical permeation enhancer applied to the nasal mucosa;
 (c) enhancing delivery of said pharmaceutical composition with phonophoresis; and,
 (d) delivering said pharmaceutical composition to a target site in the nervous system of the mammal via the nasal region.

B. The method as above at A wherein said chemical permeation enhancer is selected from the group consisting of polycationic polymers, chelators, long-chain acylcarnitines, calcium modulators, cyclodextrins, bile salts, transdermal penetration enhancers, lipophilic adjuvants, and mixtures thereof.

C. The method as above at A or B wherein said pharmaceutical composition further comprises a solvent selected from the group consisting of deionized water, an aqueous solvent and a non-aqueous solvent such as DMSO or the like.

D. The method as above at any of A–C wherein said pharmaceutical composition further comprises an additional agent, said additional agent being an anesthetic agent.

E. The method as above at any of A–D wherein said pharmaceutical composition further comprises an additional agent, said additional agent being a decongestant.

F. The method as above at any of A–E wherein said pharmaceutical composition further comprises an additional agent, said additional agent being a vasoconstrictor.

G. The method as above at any of A–F wherein said pharmaceutical composition further comprises an additional agent, said additional agent being selected from the group consisting of a decongestant, an anesthetic agent, a vasoconstrictor, and any combination of said additional agents.

H. The method as above at any of A–G wherein said chemical permeation enhancer is applied simultaneously with said pharmaceutical composition.

I. The method as above at any of A–H wherein said chemical permeation enhancer is applied, at least in part prior to administration of said pharmaceutical composition to the transnasal pathway.

J. A method of delivering a pharmaceutical composition to the central nervous system of a mammal, comprising the steps of:
 (a) administering said pharmaceutical composition transocularly;
 (b) enhancing delivery of said pharmaceutical composition with a chemical permeation enhancer applied to an ocular surface;
 (c) enhancing delivery of said pharmaceutical composition with phonophoresis; and,
 (d) delivering said pharmaceutical composition to a target site of the nervous system of the mammal via the ocular region.

K. The method as above at J wherein said chemical permeation enhancer is selected from the group consisting of polycationic polymers, chelators, long-chain acylcarnitines, calcium modulators, cyclodextrins, bile salts, transdermal penetration enhancers, lipophilic adjuvants, and mixtures thereof.

M. The method as above at J or K wherein said pharmaceutical composition further comprises a solvent selected from the group consisting of deionized water, an aqueous solvent and a non-aqueous solvent such as DMSO or the like.

N. The method as above at any of J–M wherein said pharmaceutical composition further comprises an additional agent, said additional agent being an anesthetic agent.

O. The method as above at any of J–N wherein said pharmaceutical composition further comprises an additional agent, said additional agent being a decongestant.

P. The method as above at any of J–O wherein said pharmaceutical composition further comprises an additional agent, said additional agent being a vasoconstrictor.

Q. The method as above at any of J–P wherein said pharmaceutical composition further comprises an additional agent, said additional agent being selected from the group consisting of a decongestant, an anesthetic agent, a vasoconstrictor, and any combination of said additional agents.

R. The method as above at any of J–Q wherein said chemical permeation enhancer is applied simultaneously with said pharmaceutical composition.

S . The method as above at any of J–R wherein said chemical permeation enhancer is applied, at least in part prior to administration of said pharmaceutical composition to the transocular pathway.

What is claimed is:

1. A method of delivering a pharmaceutical composition to the central nervous system of a mammal, comprising the steps of:
 (a) administering said pharmaceutical composition to the central nervous sytstem (CNS) transnasal-mucosally with electrotransport by application of an electrotransport driving force in the olfactory region to advance the composition through nasal mucosa, bypassing vasculature, to reach CNS; and
 (b) enhancing delivery of said pharmaceutical composition with a chemical permeation enhancer applied to the nasal mucosa.

2. The method as in claim 1 wherein said chemical permeation enhancer is selected from the group consisting of polycationic polymers, chelators, long-chain acylcarnitines, calcium modulators, bile salts, transdermal penetration enhancers, lipophilic adjuvants, and mixtures thereof.

3. The method as in claim 1 wherein said pharmaceutical composition further comprises a solvent selected from the group consisting of deionized water, and an aqueous-based solution and a non-aqueous solvent.

4. The method as in claim 1 wherein said pharmaceutical composition further comprises an additional agent, said additional agent being an anesthetic agent.

5. The method as in claim 1 wherein said pharmaceutical composition further comprises an additional agent, said additional agent being a decongestant.

6. The method as in claim 1 wherein said pharmaceutical composition further comprises an additional agent, said additional agent being a vasoconstrictor.

7. The method as in claim 1 wherein said pharmaceutical composition further comprises an additional agent, said additional agent being selected from the group consisting of a decongestant, an anesthetic agent, a vasoconstrictor, and any combination of said additional agents.

8. The method as in any one of claims 2–7, wherein said chemical permeation enhancer is applied simultaneously with said pharmaceutical composition.

9. The method as in any one of claims 2–7, wherein said chemical permeation enhancer is applied, at least in part prior to administration of said pharmaceutical composition to the transnasal pathway.

* * * * *